(12) United States Patent
McGowan

(10) Patent No.: US 10,874,827 B2
(45) Date of Patent: Dec. 29, 2020

(54) DETACHABLE POLYMER BOND

(71) Applicant: Boston Scientific Scimed, Inc., Maple Grove, MN (US)

(72) Inventor: Pauric John McGowan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 334 days.

(21) Appl. No.: 15/287,020

(22) Filed: Oct. 6, 2016

(65) Prior Publication Data
US 2017/0095642 A1    Apr. 6, 2017

Related U.S. Application Data

(60) Provisional application No. 62/237,914, filed on Oct. 6, 2015.

(51) Int. Cl.
| | | |
|---|---|---|
| *A61M 25/00* | (2006.01) | |
| *A61L 29/06* | (2006.01) | |
| *A61L 29/08* | (2006.01) | |
| *A61B 17/12* | (2006.01) | |
| *A61L 29/04* | (2006.01) | |
| *B29C 65/02* | (2006.01) | |
| *B29C 65/48* | (2006.01) | |
| *A61F 2/95* | (2013.01) | |
| *A61M 25/10* | (2013.01) | |
| *A61B 90/00* | (2016.01) | |

(Continued)

(52) U.S. Cl.
CPC ... *A61M 25/0045* (2013.01); *A61B 17/12022* (2013.01); *A61L 29/049* (2013.01); *A61L 29/06* (2013.01); *A61L 29/085* (2013.01); *A61M 25/0009* (2013.01); *A61M 25/0043* (2013.01); *A61M 25/0069* (2013.01); *B29C 65/02* (2013.01); *B29C 65/48* (2013.01); *A61B 17/1214* (2013.01); *A61B 17/12136* (2013.01); *A61B 17/12159* (2013.01); *A61B 2017/00526* (2013.01); *A61B 2017/12054* (2013.01); *A61B 2090/037* (2016.02); *A61F 2/2427* (2013.01); *A61F 2/95* (2013.01); *A61M 2025/1054* (2013.01); *B29L 2031/7542* (2013.01)

(58) Field of Classification Search
CPC .......... A61M 25/0045; A61M 25/0009; A61L 29/049; A61L 29/06; A61L 29/085
See application file for complete search history.

(56) References Cited

U.S. PATENT DOCUMENTS 3,482,576 A * 12/1969 Ericson .......... A61M 25/10184
604/99.01
6,063,070 A    5/2000 Eder
(Continued)

FOREIGN PATENT DOCUMENTS

| CN | 101415459 A | 4/2009 |
|---|---|---|
| CN | 102036619 A | 4/2011 |

*Primary Examiner* — Phillip A Gray
(74) *Attorney, Agent, or Firm* — Kacvinsky Daisak Bluni PLLC

(57) ABSTRACT

This disclosure concerns polymer catheter designs incorporating joints that break under tension. The joints are generally formed from two tubular elements comprising two different polymers with dissimilar thermal and/or mechanical characteristics, which are overlapped and exposed to heat and pressure. The disclosure also concerns methods of making and using such catheters, for instance to deliver medical implants.

20 Claims, 4 Drawing Sheets

(51) Int. Cl.
  *A61B 17/00* (2006.01)
  *A61F 2/24* (2006.01)
  *B29L 31/00* (2006.01)

(56) References Cited

U.S. PATENT DOCUMENTS

| | | | |
|---|---|---|---|
| 8,597,323 B1 * | 12/2013 | Plaza | A61B 17/12172 606/200 |
| 2006/0004399 A1 | 1/2006 | van Ockenburg et al. | |
| 2010/0049165 A1 | 2/2010 | Sutherland et al. | |
| 2012/0203322 A1 | 8/2012 | Eells | |

* cited by examiner

DETACHABLE POLYMER BOND

PRIORITY

This application claims the benefit of priority under 35 U.S.C. § 119 to U.S. Provisional Patent Application Ser. No. 62/237,914, filed Oct. 6, 2015, which is incorporated by reference in its entirely and for all purposes.

FIELD OF THE INVENTION

This application relates to the field of medical devices and medical procedures. More particularly, the application is related to devices and methods for the implantation of medical devices.

BACKGROUND

Small, catheter-delivered medical implants are ubiquitous in medicine and have made possible minimally invasive treatments for a variety of conditions that were previously untreatable or treated by open surgery, including sterilization, aortic valve replacement, filling of aneurysms, treatment of tumors and restoring blood flow across occluded coronary arteries.

Among the minimally invasive treatments made possible by catheter-borne implants are treatments in which a body lumen is occluded, for instance to prevent the undesired flow of bodily fluid therethrough. These so-called therapeutic embolization procedures are useful for the treatment of vascular and non-vascular conditions, such as peripheral aneurysms, arteriovenous malformation, uterine fibroids and various tumors. One commonly used agent for embolizing blood vessels is the embolic coil, a permanently implanted coiled wire structure which, when implanted into a blood vessel, occludes the vessel by causing thrombosis where it is deployed. Embolic coils may have different lengths and/or cross-sectional diameters, in order to fit into and occlude vascular structures of varying sizes. In use, the coils are delivered through a microcatheter in a narrow-diameter elongated configuration (e.g. to fit within a 3 Fr catheter lumen). Once deployed into the vessel, the coil may assume a complex 3-D shape such as a helix, a spiral, a J-shape, or a birds-nest shape, and may include thrombogenic fibers or bundles of fibers along its length to help facilitate clotting and, hence, occlusion of the body lumen into which they are deployed. Another common embolizing agent is a detachable balloon, which is delivered on or within a delivery catheter in a deflated configuration, inflated through the catheter so as to fill a portion of a lumen where occlusion is desired, then left in place after the catheter is retracted and removed.

During the implantation process, both detachable balloons and embolic coils, as well as other catheter-borne implants used outside of the field of therapeutic embolization (which are referred to collectively as "implants" hereinafter) are typically attached, connected or otherwise secured to the delivery catheter so as to prevent their migration during implantation, and are detached only after they have been positioned as desired by a user. This detachment may be facilitated by the use of an electrolytically severable link, a mechanical coupling mechanism, or in some cases by a joint within the catheter itself that opens or deforms to release the implant. While mechanical and electrolytic detachment mechanisms are commonly used and well established, they do increase the complexity of delivery catheter designs and may add to the costs of producing such catheters. By contrast, detachment mechanisms within the catheter itself are relatively less well developed: most commonly, the implant is held in place with an adhesive, or by a subassembly that attaches to a portion of the catheter where the implant will reside prior to deployment, or by splitting the catheter axially along a portion of its length that includes the distal portion engaging the implant. None of these arrangements is ideal, however, as each may add complexity (and, potentially, cost) to catheter designs, or may not be robust to kinking or to other stresses applied to the catheter during storage and use.

SUMMARY OF THE INVENTION

The present invention, in its various aspects, provides detachable polymer joints that break cleanly and circumferentially in response to the application of a tensile force above a predetermined threshold, as well as delivery catheters utilizing such joints and methods of making and using such catheters and joints.

In one aspect, the present invention relates to a catheter which includes first and second tubular members comprising first and second polymers, respectively, which polymers have different melting temperatures and/or rates of cooling (the second polymer's values are typically higher). The tubular members are arranged such that a junction where the second tubular members overlaps the first tubular member defines, at the proximal end of the second tubular member, a breakpoint at which the first and second tubular members separate upon application of a tension above a predetermined threshold. In some cases, a medical implant such as a detachable balloon, an embolic coil, an occlusive plug and/or a mechanical valve is attached to the second tubular member. The first polymer is, in some cases, is a polyether block amide (PBA) while the second polymer is, in some cases, a polyurethane. Alternatively or additionally, a first end of the second tubular member is at least partially embedded in a wall of the first tubular member. Catheters according to the embodiments presented above are useful in medicine, particularly in delivering medical implants.

In another aspect, the present invention relates to methods of making catheters such as those described above by disposing, over a mandrel, first and second tubular members comprising dissimilar first and second polymers, respectively, such that the second tubular member overlaps the first tubular member, disposing a third heat-shrinkable member over the overlapping first and second tubular members, then heating the overlapping first, second and third tubular members, thereby (a) causing the third heat-shrinkable member to shrink and apply pressure to the overlapping first and second tubular members, and (b) softening the first tubular member such that the end of the second tubular member infiltrates the first tubular member. The resultant catheter includes a breakable joint where the second tubular member has infiltrated the first tubular member. In some cases, the first polymer is a polyether block amide and/or the second polymer is a polyurethane. Optionally or additionally, the step of heating the overlapping first, second and third tubular members (a) does not include softening the second tubular member, (b) includes heating the portion of the first tubular member proximate the overlapping terminus of the second member, and/or (c) includes contacting at least one of the overlapping first, second and third tubular members with a heated body such as a heat sealer. In some cases, a heat shield is disposed near the heated body during the step of heating the overlapping first, second and third tubular members such that a portion of the first tubular element is not heated. The breakable joint in the resulting catheter can break upon the application of a tension to the catheter in excess of a predetermined threshold, such as 3 N.

In yet another aspect, the present invention relates to methods of treating patients which include inserting a catheter as described above into the body of a patient, then applying a tension to the catheter thereby separating the first and second tubular members. In some cases, the method includes positioning a medical implant (for instance, a detachable balloon, an embolic coil, an occlusive plug and/or a mechanical valve) attached to the second tubular member within the body of the patient prior to applying tension to the catheter.

DRAWINGS

Aspects of the invention are described below with reference to the following drawings in which like numerals reference like elements, and wherein.

Unless otherwise provided in the following specification, the drawings are not necessarily to scale, with emphasis being placed on illustration of the principles of the invention.

DETAILED DESCRIPTION OF THE PREFERRED EMBODIMENTS

The polymer joints described herein, and the catheter designs incorporating them, generally include a heat-bonded and pressure-treated overlap between two tubular segments comprising dissimilar polymers, such as polyurethane and polyether block amide ("PBA"), including, without limitation, PBA polymers sold under the name Pebax™, which is commercialized by Arkema, S.A. (Colombes, France). These polymers differ in their melting temperatures (about 189° C. for medium durometer (55 D) urethane versus about 170° C. for the PBA) and cooling temperatures (i.e. the temperatures at which the polymer materials begin to solidify after heating; the urethane cooling temperature is about 111° C. while the PBA cooling temperature is about 144° C.). Without wishing to be bound by any theory, the relatively higher melting and cooling temperatures of polyurethane compared to PBA are particularly useful for forming such joints, inasmuch as the two polymers do not form a homogeneous melt pool when heated, and the more rigid polyurethane may displace the softer PBA in and along the overlap when it is exposed to increased temperature and pressure such that, when the overlap is cooled, the resulting joint breaks cleanly when a threshold tension is applied.

Figure 1:
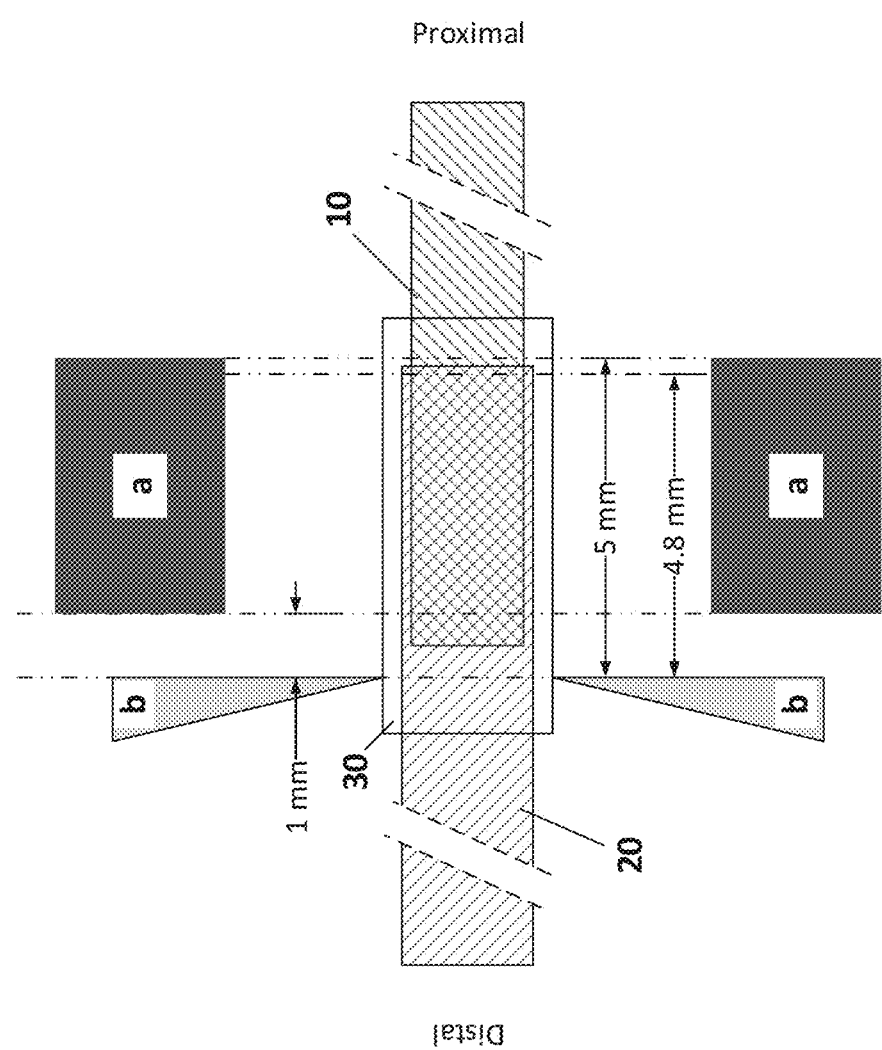
FIG. 1 shows a schematic side view of a mechanical system for forming a polymer joint according to certain embodiments of the present invention.

Turning to FIG. 1, one exemplary system production method for joints of the present invention involves forming an overlap between an inner segment 10 of tubing, preferably comprising PBA, and a separate outer segment 20 of tubing, preferably comprising polyurethane. This overlap is formed as the two segments 10, 20 are positioned over a mandrel (not shown in FIG. 1 for clarity), which mandrel is preferably lubricated or includes a lubricious coating to facilitate its removal from the tubing following formation of the joint. Over the joint, a segment of heat-shrink tubing 30 is positioned, so as to apply pressure to the joint during and after the heating process. A heating element a, such as a constant heat sealer is positioned over the joint so as to apply heat to the overlap, and a heat shield b is optionally (but not necessarily) positioned distally (i.e. toward the far end of the outer segment 20) of the heating element a to protect any structures that may be damaged by the application of heat. The temperature of the heating element is selected to be above the melting point of at least one of the polymer segments 10, 20 and above the temperature necessary to shrink the heat-shrink tubing 30. Heat is applied to the joint for an interval sufficient to cause softening of the inner segment 10 without melting fully.

Figure 2A:
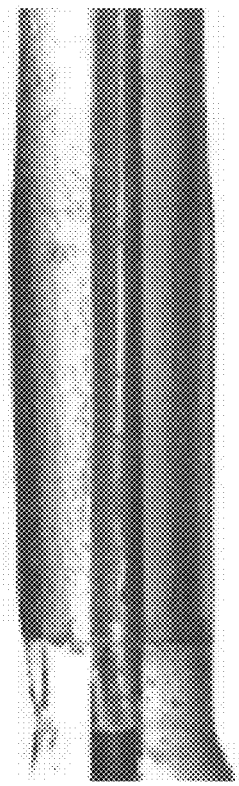
FIG. 2A shows a photograph of an exemplary catheter comprising a polymer joint.
Figure 2B:
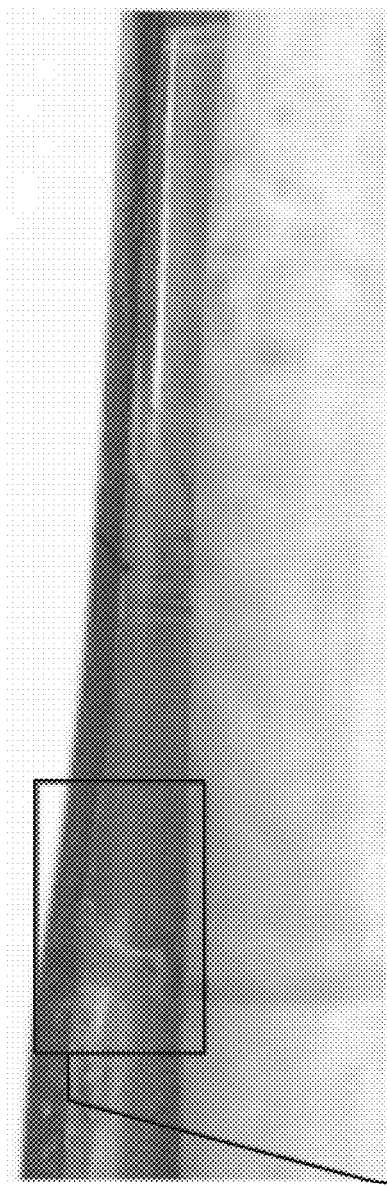
FIG. 2B shows an enlarged view of the catheter and joint of FIG. 2A.
Figure 2C:
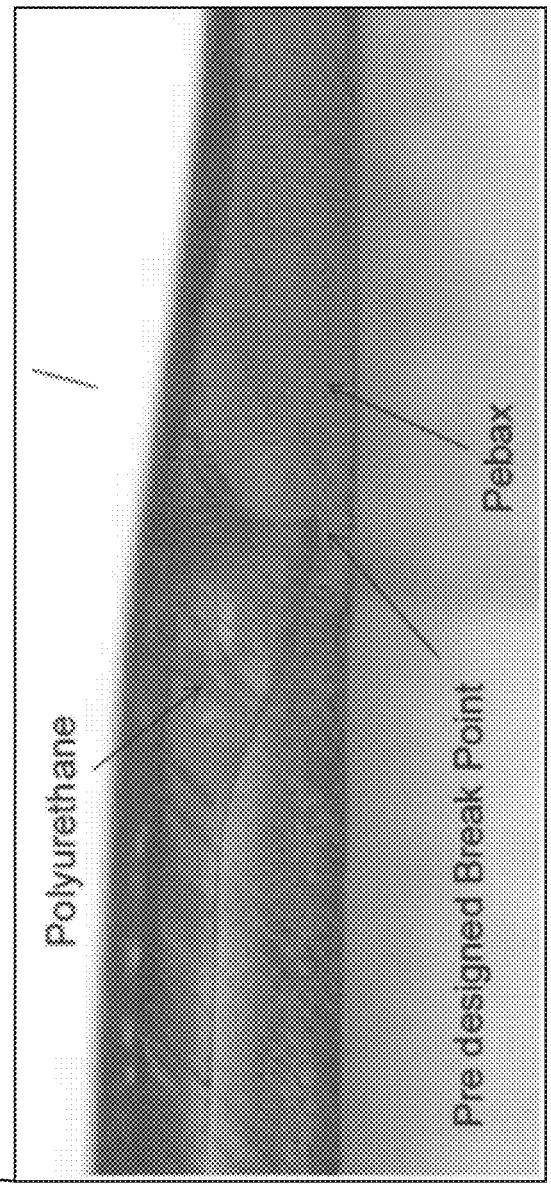
FIG. 2C shows an enlarged view of the region of interest shown in FIG. 2B including the polymer joint.
Figure 3A:
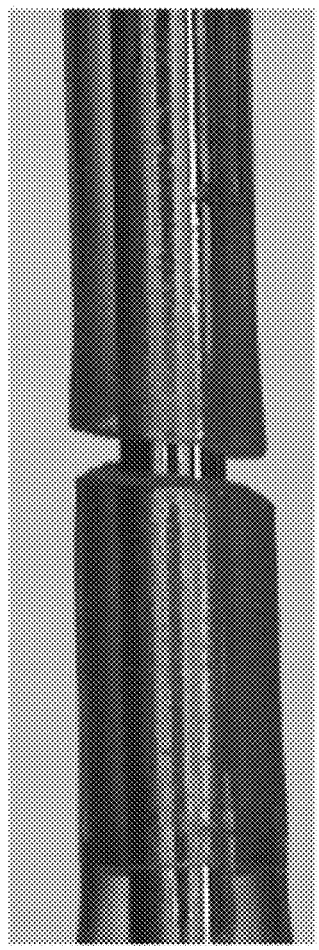
FIG. 3A shows a photographic side view of an exemplary catheter incorporating a polymer joint that has been severed.
Figure 3B:
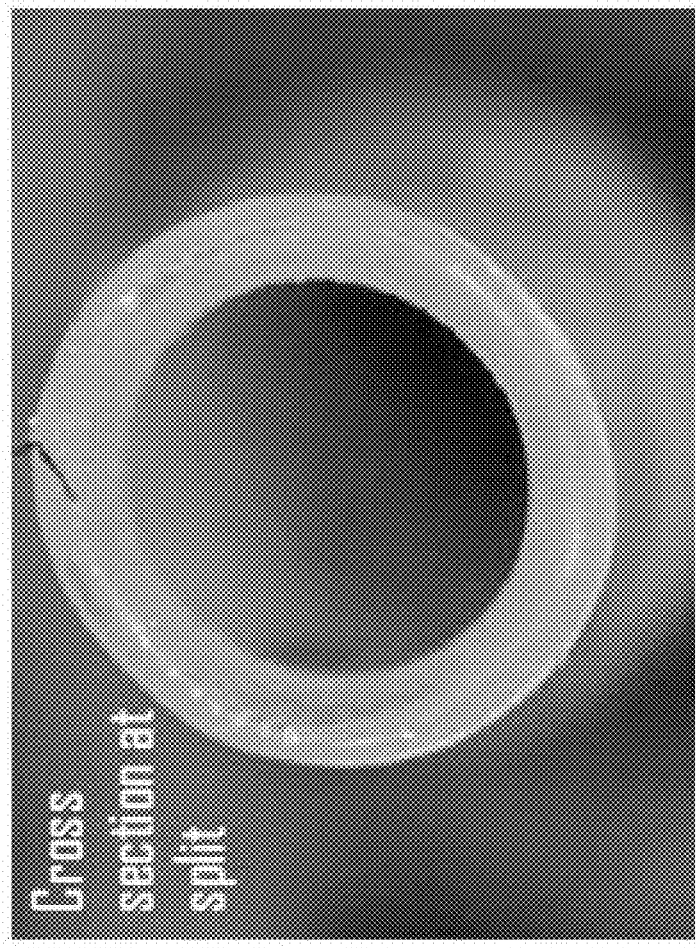
FIG. 3B shows a photographic view of a severed end of the joint in FIG. 3A.

In the examples shown in FIGS. 2 and 3, the heating element was a constant heat sealer (Hot Jaw™ IMPAK Corporation, Los Angeles, Calif. with a surface temperature of 450° C., though in other embodiments heating is provided by optical (e.g. laser) or electromagnetic (e.g. induction) mechanisms currently used in the art such as the induction systems commercialized by PlasticWeld Systems, Inc. (Newfane, N.Y.). Whatever form of heating element is used, it is preferably able to provide relatively focused heat encompassing the overlap between the inner segment 10 and proximal end of the outer segment 20 and to provide heating over an interval and at a suitable temperature to avoid melting or degradation of the outer segment 20 and/or the heat-shrink tubing 30 while causing sufficient deformation of the inner and/or outer segments 10, 20 to form a satisfactory joint.

With respect specifically to the positioning of the heating element a relative to the joint, FIG. 1 illustrates one preferred arrangement in which the proximal end of the outer segment 20 is positioned within, but near the margin of, the area to be heated by the heating element a. For instance, where the heating element a is 4 mm across, and the optional heat shield b is positioned approximately 1 mm distally to the heating element a, to provide additional thermal protection of elements such as balloons at the distal end of the assembly. In the pictured arrangement, the proximal end of the outer tube 20 is positioned between 4.8 and 5.0 mm from the inner edge of the heat shield b, resulting in proximal end of the overlapping outer segment 20 sitting about 0.2 mm from the proximal edge of the heating element a. More generally, the proximal end of the outer tubular segment 20 is less than 0.2 mm, 0.3 mm, 0.5 mm, 0.75 mm, 1.0 mm, 1.5 mm, 2.0 mm, etc. from the proximal edge of the heating element a. This positioning allows softening of the inner tube 10 about the proximal end of the outer tube 20, while constraining the region of inner tube 10 that is softened to roughly coincide with the portion covered by, and therefore reinforced by, the outer tube 20, thereby avoiding the potential for melting and/or weakening of the inner tube proximal to the joint.

Following heating, the resulting joint is cooled, the shrink-wrap 30 and/or the mandrel are removed, and the joined segments are further processed for form a catheter having the desired dimensions and characteristics. As shown in FIG. 2, the resulting joint includes, at its proximal end (and near the proximal end of the outer tube 20), a linear junction between the inner and outer polymer materials. FIGS. 2B and 2C illustrate that the proximal end of the outer tube 20 has deformed and infiltrated the inner tube 10.

Turning now to FIG. 3, when sufficient tension is applied to a catheter comprising a joint according to the embodiments of the present invention, it breaks cleanly at the linear junction as illustrated in FIGS. 3A and B. In the example shown in FIG. 3, the applied tension is 10- N, though the force required to break the joint can be reduced significantly by reducing the thickness of the inner segment 10 and/or the outer segment 20, as well as by increasing the time or temperature used during the formation process, thereby increasing the degree of deformation and/or melting at the joint. In preferred embodiments, the force required to separate the joint is around 3-7 N, (e.g. 3 N, 4 N, 5 N, 6 N, 7 N, etc.) The force necessary to separate the joint will generally be chosen based on the application, including the size and robustness of the body lumen into which the implant will be deployed and the robustness of the implant being delivered.

Polymer joints according to the present invention are useful in a variety of catheter-based applications. In preferred cases, the joint will be positioned at or near a distal end of a delivery catheter for an implant such as an embolic coil, a detachable embolization balloon, a cardiac valve, a stent, etc. In use, the delivery catheter is inserted into the body of the patient and its distal end is positioned at or near a site where treatment and/or delivery of the implant is desired. Following insertion of the implant (such as inflation of a balloon, or expansion of a collapsible element such as a stent, embolic coil, or valve), tension is applied to the proximal end of the catheter while the distal end is held in place, for instance by the expanded and deployed implant, or by means of a rigid wire or other element inserted into the catheter which applies a force in the opposite direction from which the tension is applied to the proximal end. Without being bound by any theory, during the application of tension, stress accumulates at the joint until breakage occurs. Thereafter, the proximal portion of the catheter (along with any other elements not being implanted) are retracted, leaving the implant within the body of the patient.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have been described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A catheter, comprising:
    a first tubular member comprising a first polymer; and
    a second tubular member joined to the first member, the second tubular member comprising a second polymer having at least one of a higher melting temperature and a lower cooling temperature than the first polymer;
    wherein a junction between the first and second tubular members is configured such that the second tubular member overlaps in contact with the first tubular member, the junction forming a wall of the catheter having a first portion of the catheter wall outside of the junction comprising the first tubular member, a second portion of the catheter wall outside of the junction comprising the second tubular member, and a third portion of the catheter wall between the first portion and the second portion comprising both the first tubular member and the second tubular member; and
    wherein the proximal end of the second tubular member defines a point at which the first and second tubular members separate upon the application of a tension above a predetermined threshold.

2. The catheter of claim 1, further comprising a medical implant attached to the second tubular member.

3. The catheter of claim 2, wherein the medical implant is selected from the group consisting of a detachable balloon, an embolic coil, an occlusive plug and a mechanical valve.

4. The catheter of claim 1, wherein the first polymer is a polyether block amide (PBA).

5. The catheter of claim 4, wherein the second polymer is a polyurethane.

6. The catheter of claim 1, wherein the third portion comprises the second polymer of the second tubular member at least partially embedded in the first polymer of the first tubular member.

7. A method of treating a patient comprising the steps of:
    inserting, into a body of the patient, a catheter, comprising:
    a first tubular member comprising a first polymer; and
    a second tubular member, the second tubular member comprising a second polymer having at least one of a higher melting temperature and a higher rate of cooling than the first polymer;
    wherein a junction between the first and second tubular members is configured such that the second tubular member overlaps in contact with the first tubular member, the junction forming a wall of the catheter having a first portion of the catheter wall outside of the junction comprising the first tubular member, a second portion of the catheter wall outside of the junction comprising the second tubular member, and a third portion of the catheter wall between the first portion and the second portion comprising both the first tubular member and the second tubular member; and wherein the junction of the catheter wall between the second portion and the third portion defines a point at which the first and second tubular members separate upon the application of a tension above a predetermined threshold; and applying a tension to the catheter, thereby separating the first and second tubular members.

8. The method of claim 7, wherein the method includes positioning a medical implant attached to the second tubular member within the body of the patient prior to applying tension to the catheter.

9. The method of claim 8, wherein the medical implant is selected from the group consisting of a detachable balloon, an embolic coil, an occlusive plug and a mechanical valve.

10. The method of claim 7, wherein the first polymer is a polyether block amide (PBA).

11. The method of claim 10, wherein the second polymer is a polyurethane.

12. The method of claim 7, wherein third portion comprises the second polymer of the second tubular member at least partially embedded in the first polymer of the first tubular member.

13. A method of making a catheter, comprising the steps of:

disposing, over a mandrel, first and second tubular members comprising dissimilar first and second polymers, respectively, such that a portion of the second tubular member overlaps in contact with a portion of the first tubular member to form a junction;

disposing a third tubular member over the overlapping portions of the first and second tubular members;

heating the overlapping first, second and third tubular members, thereby (a) causing the third tubular member to shrink and apply pressure to the overlapping portions of first and second tubular members, and (b) softening the overlapping portion of the first tubular member such that the second polymer of the second tubular member at least partially embeds in the first polymer of the first tubular member; and wherein the junction forms a wall of the catheter having a first portion of the catheter wall outside of the junction comprising the first tubular member, a second portion of the catheter wall outside of the junction comprising the second tubular member, and a third portion of the catheter wall between the first portion and the second portion comprising the overlapping portions of the first tubular member and the second tubular member.

14. The method of claim 13, wherein the first polymer is a polyether block amide.

15. The method of claim 14, wherein the second polymer is polyurethane, and wherein the step of heating the overlapping first, second and third tubular members does not include softening the second tubular member.

16. The method of claim 13, wherein the step of heating the overlapping first, second and third tubular members includes deforming the first tubular member more than the second tubular member.

17. The method of claim 13, wherein the junction at a point between the second portion and the third portion breaks upon the application of a tension to the catheter in excess of a predetermined threshold.

18. The method of claim 13, wherein the step of heating the overlapping first, second and third tubular members includes contacting at least one of the overlapping first, second and third tubular members with a heated body.

19. The method of claim 18, wherein the heated body is a heat sealer.

20. The method of claim 18, wherein a heat shield is disposed near the heated body during the step of heating the overlapping first, second and third tubular members such that a portion of the first tubular member is not heated.

* * * * *